United States Patent [19]

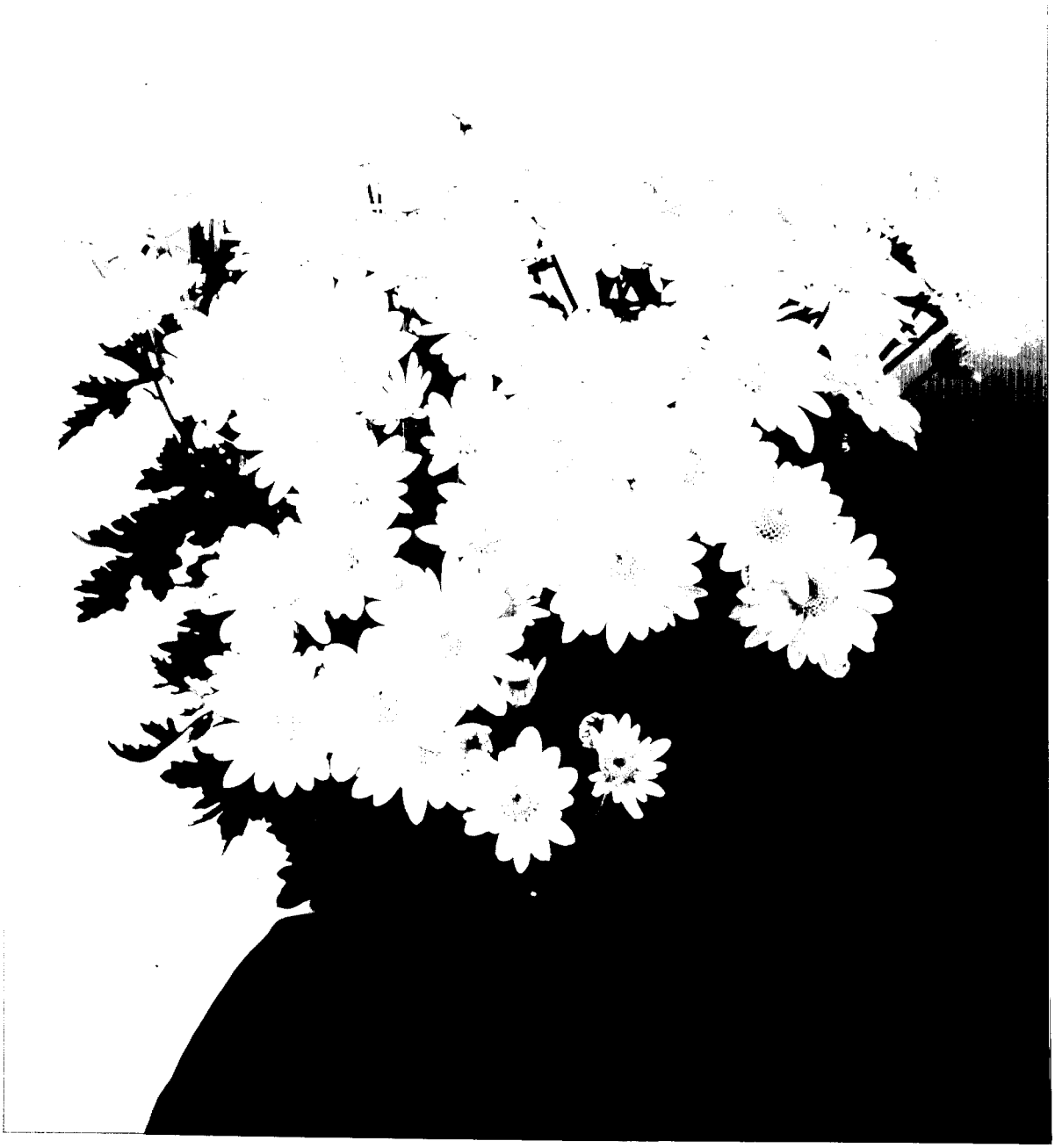

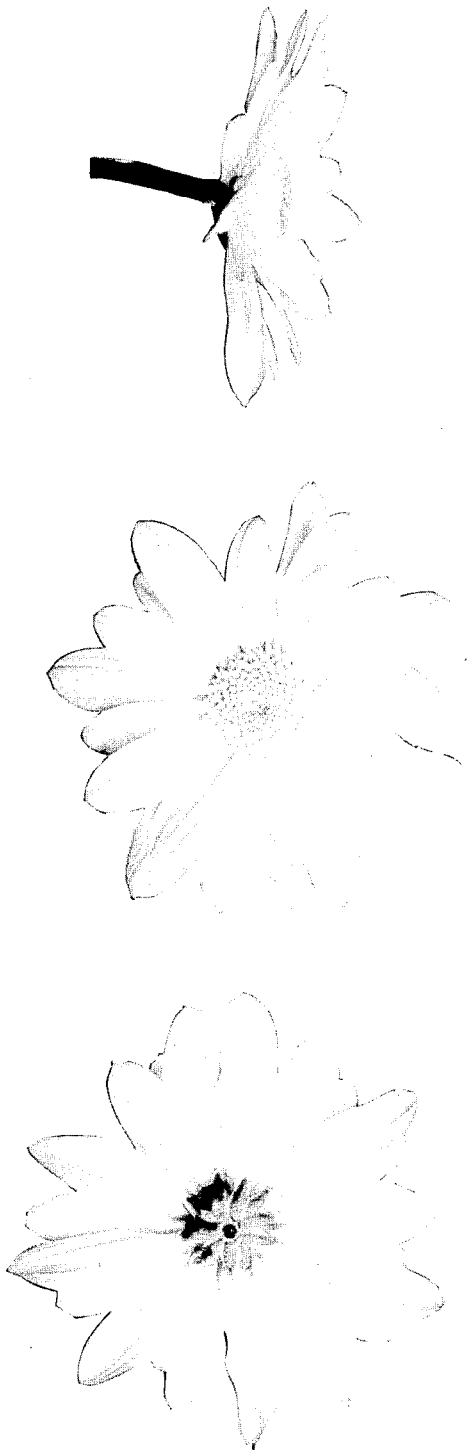

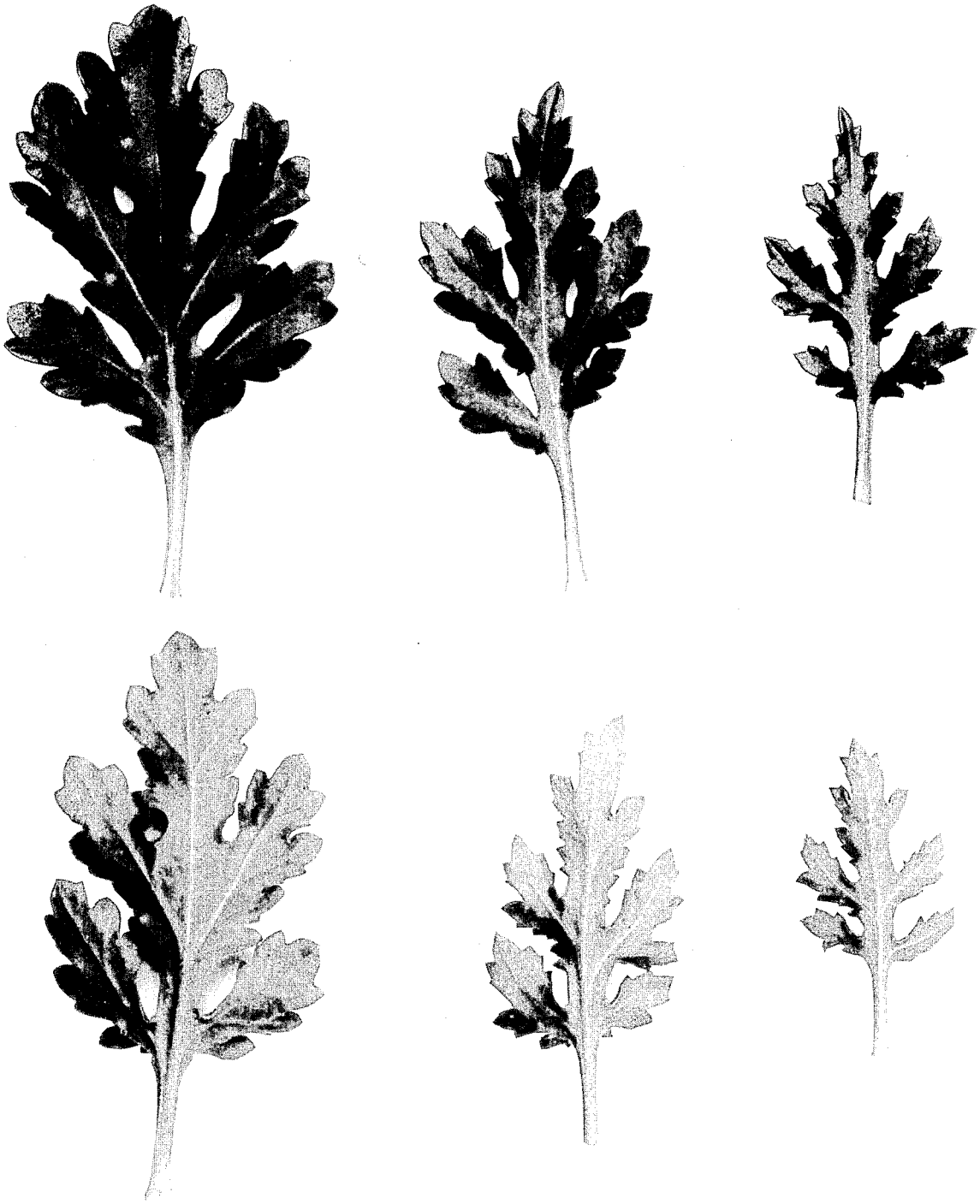

Duffett

[11] Patent Number: Plant 5,779

[45] Date of Patent: Aug. 12, 1986

[54] CHRYSANTHEMUM PLANT NAMED REJOICE

[75] Inventor: William E. Duffett, Salinas, Calif.

[73] Assignee: Yoder Brothers, Inc., Barberton, Ohio

[21] Appl. No.: 675,566

[22] Filed: Nov. 28, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Rejoice having flat capitulum form; anemone capitulum type; yellow ray floret color; diameter across face of capitulum ranging from 6 to 8 cm. at maturity; uniform eight week photoperiodic flowering response to short days; medium plant height when grown as a pinched, spray pot mum; semi-spreading branching pattern, and tolerance of high summer 21° C. night to 37° C. day temperatures for bud initiation and flower development.

3 Drawing Figures

The present invention comprises a new and distinct cultivar of *Chrysanthemum morifolium*, Ramat., named Rejoice.

Rejoice is a product of a planned breeding program which had the objective of creating new chrysanthemum cultivars for pinched spray pot mum programs having anemone capitulum type, yellow floret color, eight week flowering response and the ability to produce commercially acceptable quality in year round programs. Such traits in combination were not present or required improvements in previously available commercial cultivars.

Rejoice was originated from a cross made by William E. Duffett in a controlled breeding program in Salinas, Calif. in 1978. The precise identification of the male and female parents has been lost and is classified as unknown.

Rejoice was discovered and selected as one flowering plant within the progeny of the stated cross by William E. Duffett in 1979 in a controlled environment in Salinas, Calif.

The first act of asexual reproduction of Rejoice was accomplished when vegetative cuttings were taken from the initial selection in 1979 in a controlled environment in Salinas, Calif. by a technician working under formulations established and supervised by William E. Duffett. Horticultural examination of selected units initiated February 1982 has demonstrated that the combination of characteristics as herein disclosed for Rejoice are firmly fixed and are retained through successive generations of asexual reproduction.

Rejoice has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Rejoice which in combination distinguish this chrysanthemum as a new and distinct cultivar:

(1) Flat capitulum form.

(2) Anemone capitulum type.

(3) Yellow ray floret color.

(4) Diameter across face of capitulum ranging from 6 to 8 cm. at maturity.

(5) Uniform eight week photoperiodic flowering response to short days.

(6) Medium plant height, requiring 2 long day weeks prior to pinch and short days, and 1–2 applications of 2500 ppm B-9 SP, the first at 14, the second at 21 days after the beginning of short days to attain a flowered plant height of 25 to 35 cm. in 6″ pots.

(7) Semi-spreading branching pattern.

(8) Tolerance of high summer 21° C. night to 37° C. day temperatures.

The accompanying photographic drawings depict typical leaf and inflorescence characteristics of Rejoice. Sheet 1 is a color photograph of a plant of Rejoice grown as a pinched, spray pot mum, with colors being as accurate as possible with renditions of this type. Sheet 2 is a black and white photograph of three views of the inflorescence of Rejoice. Sheet 3 shows the upper and under surface of the leaves of Rejoice in three stages of development (mature, intermediate and immature).

Of the many commercial cultivars known to the present inventor the most similar in comparison to Rejoice is the parent cultivar Pert, disclosed in U.S. Plant Pat. No. 4,764. Reference is made to attached Chart A which compares certain characteristics of Rejoice to those same characteristics of Pert.

The capitulum type of Rejoice is anemone. The tubular disc development forming the cushion is scant, restricted and crested, more closely resembling the daisy type of Pert than the true anemone. Pollen is produced abundantly by Rejoice; scant to none by Pert. Inflorescense color of Pert is darker. Plant height of Pert is shorter. Rejoice has superior tolerance of high temperature. Similar traits are the branching pattern, diameter of capitulum and flowering response. The corolla of disc florets of Rejoice develops and retains a more intense green eye.

In the following description, color references are made to The Royal Horticultural Society Colour Chart. The color values were determined between 10:00 and 10:15 a.m. on June 19, 1984 under 380 foot-candle light intensity at Salinas, Calif.

Classification:

*Botanical.*—*Chrysanthemum morifolium,* Ramat., cv Rejoice.

*Commercial.*—Anemone spray pot mum.

I. INFLORESCENCE

A. Capitulum:

*Form.*—Flat.

*Type.*—Anemone.

*Diameter across face.*—6 to 8 cm.

B. Corolla of ray florets:

*Color (General tonality from a distance of three meters).*—Yellow.

*Color (upper surface).*—6A, 6B.

*Color (under surface).*—6C.

*Shape.*—Oblong, rounded tip.

C. Corolla of disc florets:

*Color (mature).*—5A, 5B.

*Color (immature).*—154A, 154B.

D. Reproductive organs:

*Androecium.*—Present disc florets only; abundant pollen.

*Gynoecium.*—Present both ray and disc florets.

II. PLANT

A. General appearance:

*Height.*—Medium.

*Branching pattern.*—Semi-spreading.

B. Foliage:

*Color (upper surface).*—147A.

*Color (under surface).*—147B.

*Shape.*—Deeply lobed, and finely cut with broad deep serration.

CHART A

COMPARISON OF REJOICE AND PERT

| CULTIVAR | RAY FLORET COLOR | CAPITULUM FORM AND TYPE | BRANCHING PATTERN | DIAMETER ACROSS FACE OF CAPITULUM |
|---|---|---|---|---|
| REJOICE | YELLOW | FLAT ANEMONE | SEMI-SPREADING | 6 to 8 cm. |
| PERT | DARK YELLOW | FLAT | SEMI-SPREADING | 7 to 9 cm. |

| CULTIVAR | PLANT HEIGHT | FLOWERING RESPONSE PERIOD | TEMPERATURE TOLERANCE |
|---|---|---|---|
| REJOICE | MEDIUM | 8 WEEKS | STRONG TOLERANCE OF HIGH TEMPERATURES |
| PERT | SHORT | 8 WEEKS | SLIGHT TOLERANCE OF HIGH TEMPERATURES |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Rejoice, as described and illustrated, and particularly characterized as to uniqueness by the combined characteristics of flat capitulum form; anemone capitulum type; yellow ray floret color; diameter across face of capitulum ranging from 6 to 8 cm. at maturity; uniform eight week flowering response; medium plant height; semi-spreading branching pattern; and tolerance of high summer 21° C. night to 37° C. day temperatures for bud initiation and flower development.

* * * * *